United States Patent
Barrera

(10) Patent No.: US 11,497,502 B2
(45) Date of Patent: Nov. 15, 2022

(54) SURGICAL STAPLER APPARATUS AND METHOD

(71) Applicant: HUGO BARRERA, M.D., INC., Chula Vista, CA (US)

(72) Inventor: Hugo Barrera, Chula Vista, CA (US)

(73) Assignee: HUGO BARRERA, M.D., INC, Chula Vista, CA (US)

( * ) Notice: Subject to any disclaimer, the term of this patent is extended or adjusted under 35 U.S.C. 154(b) by 607 days.

(21) Appl. No.: 16/480,662

(22) PCT Filed: Jan. 19, 2018

(86) PCT No.: PCT/US2018/014529
§ 371 (c)(1),
(2) Date: Jul. 24, 2019

(87) PCT Pub. No.: WO2018/140324
PCT Pub. Date: Aug. 2, 2018

(65) Prior Publication Data
US 2021/0128152 A1 May 6, 2021

Related U.S. Application Data

(60) Provisional application No. 62/449,940, filed on Jan. 24, 2017.

(51) Int. Cl.
*A61B 17/115* (2006.01)
*A61M 13/00* (2006.01)
*A61B 17/00* (2006.01)

(52) U.S. Cl.
CPC ....... *A61B 17/1155* (2013.01); *A61M 13/003* (2013.01); *A61B 2017/00818* (2013.01); *A61M 2205/075* (2013.01); *A61M 2205/3337* (2013.01); *A61M 2210/1067* (2013.01)

(58) Field of Classification Search
CPC . A61B 17/1155; A61B 17/068; A61B 17/072; A61M 13/003
See application file for complete search history.

(56) References Cited

U.S. PATENT DOCUMENTS

| | | | | |
|---|---|---|---|---|
| 5,139,478 A | * | 8/1992 | Koninckx | A61M 13/003 600/560 |
| 5,514,087 A | | 5/1996 | Jones | |
| 9,265,503 B2 | * | 2/2016 | Vestweber | A61B 17/105 |

(Continued)

OTHER PUBLICATIONS

International Search Report for related International Application No. PCT/US2018/14529, dated Apr. 9, 2018; 1 page.

*Primary Examiner* — Nathaniel C Chukwurah
(74) *Attorney, Agent, or Firm* — Procopio, Cory, Hargreaves & Savitch LLP

(57) ABSTRACT

A surgical stapler apparatus or assembly comprises a surgical stapler device having an internal channel extending from a stapler actuating handle to a stapler head of the device and a gas insufflation device having a pressurized gas supply connected to the internal channel of the stapler device via an inlet port at a handle portion intersecting with the channel in order to supply pressurized gas to the channel as the stapler shaft is inserted into the lumen of a colon, rectum or the like. Pressurized gas travels along the channel and out of the stapler head at the distal end of the stapler device in order to inflate the lumen ahead of the advancing stapler head, easing insertion.

6 Claims, 5 Drawing Sheets

(56) References Cited

U.S. PATENT DOCUMENTS

| | | |
|---|---|---|
| 2005/0059992 A1 | 3/2005 | Leiboff |
| 2006/0052771 A1 | 3/2006 | Sartor et al. |
| 2007/0265492 A1* | 11/2007 | Sonnenschein .......... A61B 1/12 600/101 |
| 2008/0004566 A1 | 1/2008 | Sloan |
| 2010/0163598 A1* | 7/2010 | Belzer ................ A61B 17/1155 227/181.1 |
| 2011/0218484 A1* | 9/2011 | Zemlok .............. A61B 17/3474 604/26 |
| 2015/0133779 A1 | 5/2015 | Yurek et al. |

* cited by examiner

SURGICAL STAPLER APPARATUS AND METHOD

BACKGROUND

Related Field

The subject matter discussed herein relates generally to surgical anastomosis equipment and methods, and particularly to surgical staplers used primarily for gastrointestinal anastomoses as a part of intestinal surgery.

Related Background

End-to-end anastomosis staplers, also known as EEA staplers, are used for stapling together generally circular end portions of the rectum, colon, small bowel, stomach and esophagus following surgery. Such devices have handles including a staple actuator and an elongated stapler shaft extending from the handle and designed to be inserted through the lumen of the organ which is to be stapled. The distal end of the EEA stapler has a stapler head or cartridge and an anvil movable relative to the head between an advanced position spaced from the head and a retracted, stapling position in which opposing, generally annular, cut end portions of the organ to be stapled are gripped between opposing end faces of the head and anvil. The anvil is secured at the end of a retractable anvil stem. After insertion of the stapler shaft into the rectum, colon or the like and retraction in to the gripping position ready for stapling once the end portions of the cut organ are suitably secured to the head and anvil, respectively, and actuator in the handle is activated to fire the stapler head to secure end portions of the rectum, colon or the like together with a circle of staples.

Trans rectal introduction of such staplers can sometimes prove challenging given the presence of rectal valves that can sometimes impede introduction of the stapler to the required location, particularly if the rectum needs to be traversed. The design of the stapler itself can add to this problem since it has sharp angles at the stapler end portion which needs to be introduced. In some cases, surgeons use graduated dilating instruments which are sequentially introduced trans-rectally in progressively larger sizes to stretch open the rectal valves prior to introducing the stapler. This further increases the time required for the procedure.

SUMMARY

In one embodiment, a surgical stapler apparatus has a handle portion including a staple actuator, an elongate portion extending from the handle portion and designed to be inserted through the lumen of the organ which is to be stapled, a stapler head at a distal end of the elongate portion and an anvil movably mounted at the stapler head and movable relative to the head between an advanced condition spaced from the head and a retracted, stapling position configured to grip end portions of a lumen to be stapled, the handle portion having a gas or air inlet port in communication with an internal channel extending from the handle portion to the stapler head, and an air insufflation device comprising a gas supply tube having a first end in sealing engagement with the inlet port in the handle portion and a supply of pressurized gas or air in communication with the gas supply tube. The supply of pressurized gas or air may comprise a manually operated inflation bulb or pump or a pressurized gas supply which does not require manual pumping.

In one embodiment, an existing surgical stapler apparatus is retrofitted to add the gas supply inlet port in communication with the existing stapler channel. No modification to the stapler shaft or channel itself is required, other than the addition of the gas inlet port extending transversely through the wall of the handle portion to intersect the channel or lumen extending from the handle to the stapler head of the apparatus. An on-off valve at the inlet port may be provided to open automatically in response to gas pressure and to close when the pressurized gas supply is stopped or disconnected.

The air insufflation device attached to the proximal or handle end of the stapler apparatus allows air to be introduced through the channel of the stapler shaft up to the distal end, where it exits through the end of the stapler head or stapler base. The pressurized gas blown into the rectal lumen stretches the rectum and rectal valves open, reducing the risk of impeding introduction of the stapler shaft to the desired location or of sharp angles at the stapler head being hung up or snagged by the rectal valves, and generally allowing for smoother introduction of the stapler head and shaft along the rectum or other passageway. This may avoid the need to use gradual dilating instruments to open the passage in advance of introduction of the stapler.

Since the air inflation device uses the existing passageway or channel along the stapler shaft for introducing pressurized air into the lumen of the rectum or other abdominal organ, there is no need to modify the internal design of the stapler itself to allow for air insufflation. Thus, the air insufflation device may be readily retrofitted onto a pre-existing EEA stapler, by drilling an air insufflation port into the handle end portion of the pre-existing stapler and attaching the external tubing with the manual bulb pump or other pressurized air source.

According to another aspect, the integrity of an anastomosis of the colon or rectum after firing the stapler may be tested by supplying pressurized air to the stapler shaft channel from the pressurized air supply via the supply tube. If no air bubbles are seen at the anastomosis site, then the anastomosis may be considered intact. A pressure relief valve may be provided in the insufflator air supply tube and configured to cut off supply of gas to the stapler channel if the air pressure exceeds a predetermined maximum value, such as 25 mm. Hg, so as to avoid or reduce the risk of over-inflation of the rectum or colon, which may otherwise result in tearing the staple line at the end of the rectum.

BRIEF DESCRIPTION OF THE DRAWINGS

The details of various embodiments can be gleaned in part from a study of the accompanying drawings, in which like reference numbers refer to like parts, and in which.

DETAILED DESCRIPTION

Figure 1:
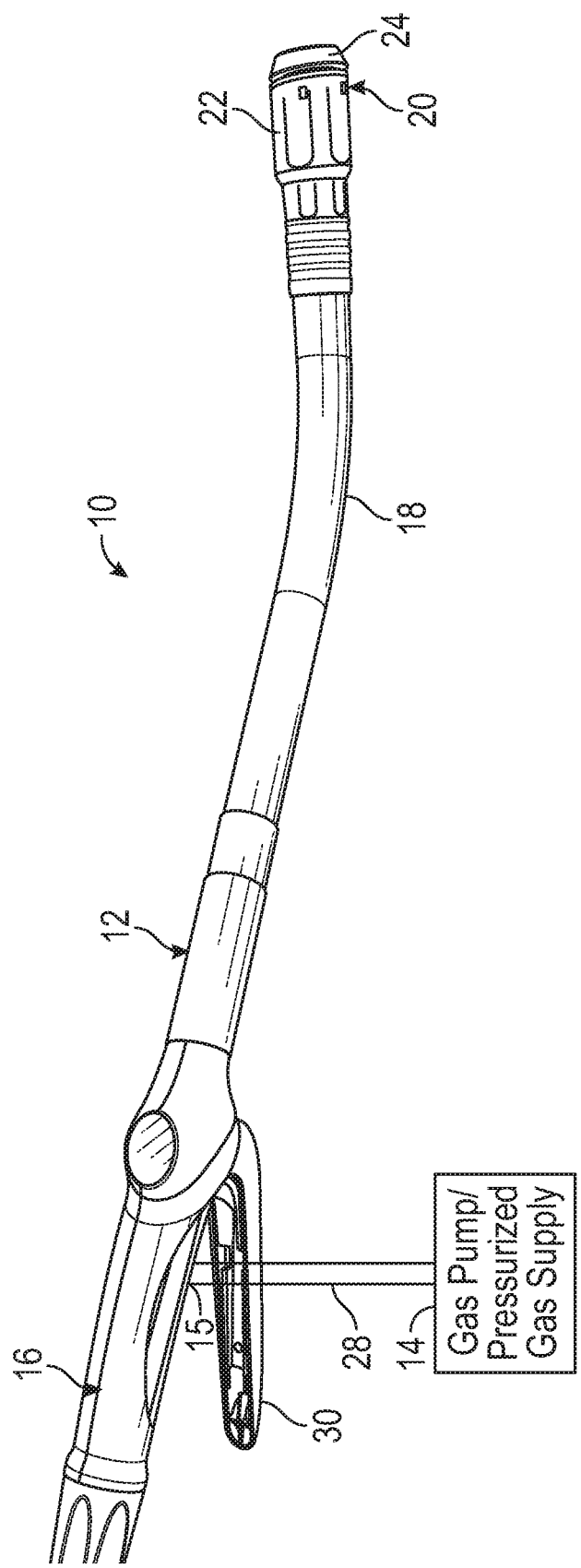
FIG. 1 is a perspective view illustrating one embodiment of an anastomosis surgical stapler apparatus including an air insufflation device.

Certain embodiments as described herein are generally concerned with end-to-end anastomosis staplers for use in gastrointestinal surgery, and provide for a circular, end-to-end stapler apparatus including an insufflation device having a pressurized gas supply and a gas or air hose extending from the gas supply and secured to an inlet port at or adjacent the handle portion of the stapler apparatus in communication with an existing channel extending from the handle portion through the stapler shaft to the stapler head, to allow for insufflating the rectum, colon or like with air in advance of the stapler head during insertion of the stapler shaft to a stapling location.

The subject matter described herein is taught by way of example implementations. Various details have been omitted for the sake of clarity and to avoid obscuring the subject matter. The examples shown below are directed to devices, systems and methods for providing a combined surgical stapler and gas insufflator apparatus. Features and advantages of the subject matter should be apparent from the following description.

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation.

FIGS. 1 to 5 illustrate one embodiment of a combined surgical stapler and gas insufflator apparatus or assembly 10 which comprises an end-to-end anastomosis or EEA stapler device 12 and an insufflation device comprising a pressurized air or gas supply 14 and an air input tube 28 connected between gas supply 14 and a gas supply inlet port 15 at the handle portion 16 of stapler device 12. The EEA stapler device 12 may be any conventional EEA stapler having an interior channel extending from the handle to the stapler head assembly, such as the Ethicon Endosurgery ILS™ 25 manufactured by Ethicon, Inc. of Somerville, N.J., or other similar devices, and therefore will not be described in detail.

Figure 2:
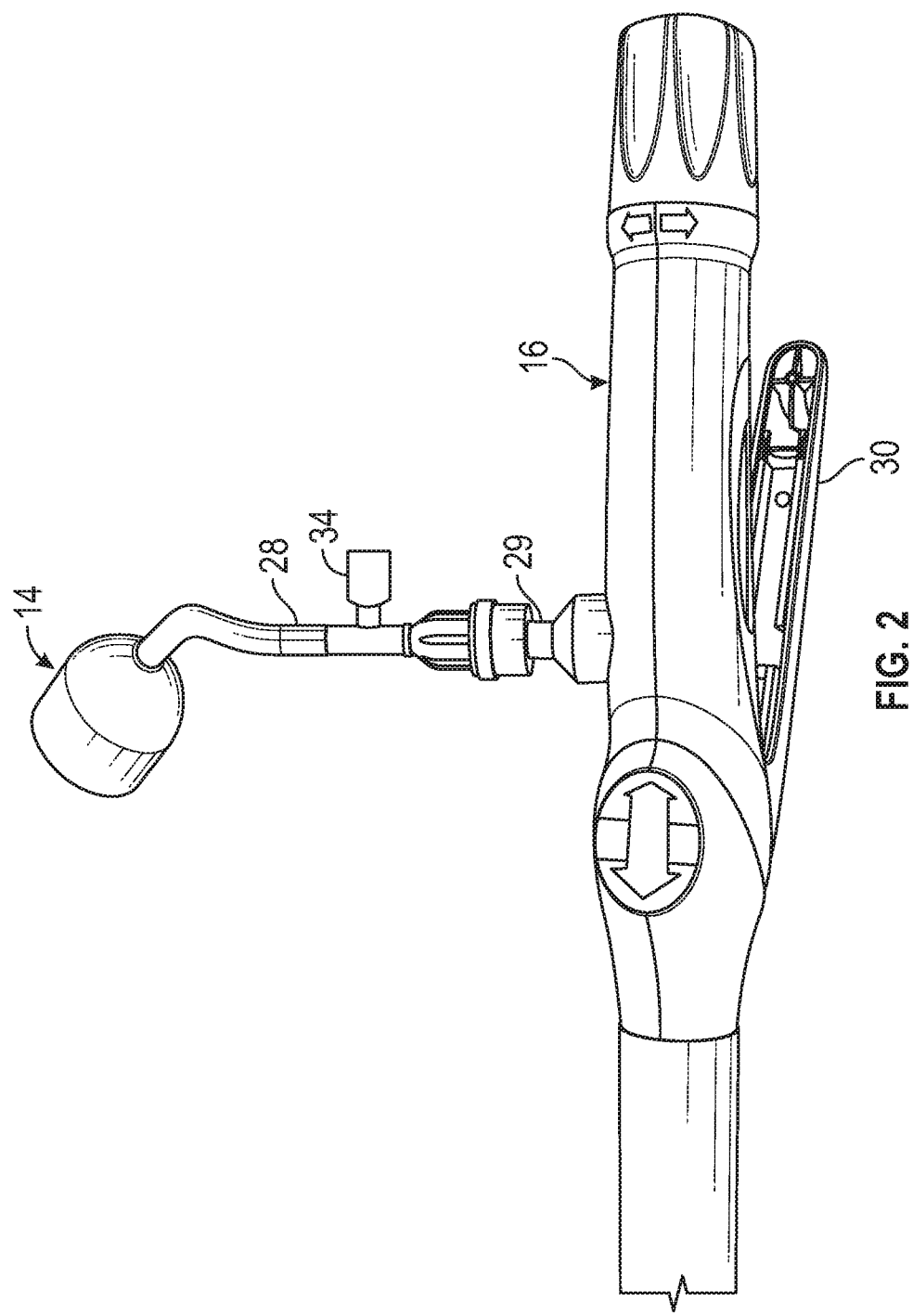
FIG. 2 is a perspective, cut-away view of the handle portion of the apparatus of FIG. 1.
Figure 3:
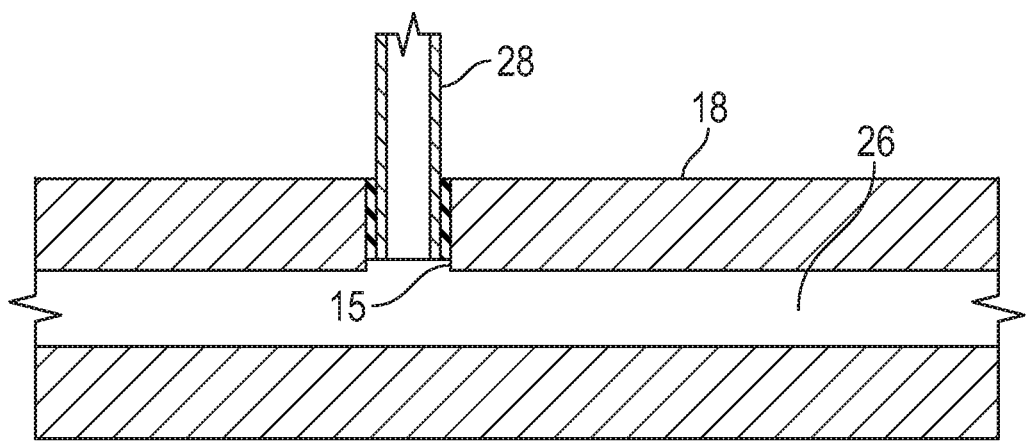
FIG. 3 is a longitudinal cross-sectional view of part of the handle of the stapler apparatus, illustrating the connection of air supply tube to an inlet port connected to the existing stapler channel.
Figure 4:
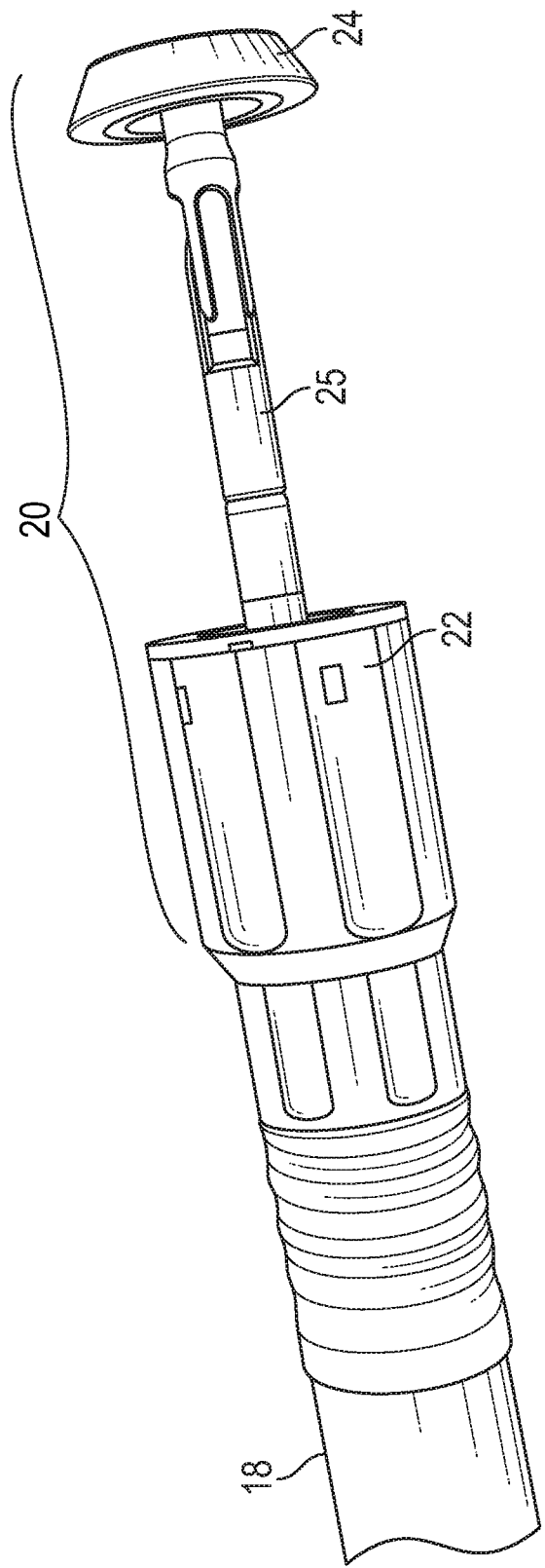
FIG. 4 is a perspective view of the stapler head of FIG. 1 in an extended condition in which the anvil and anvil stem or shaft of the stapler extend out of the stapler base.
Figure 5:
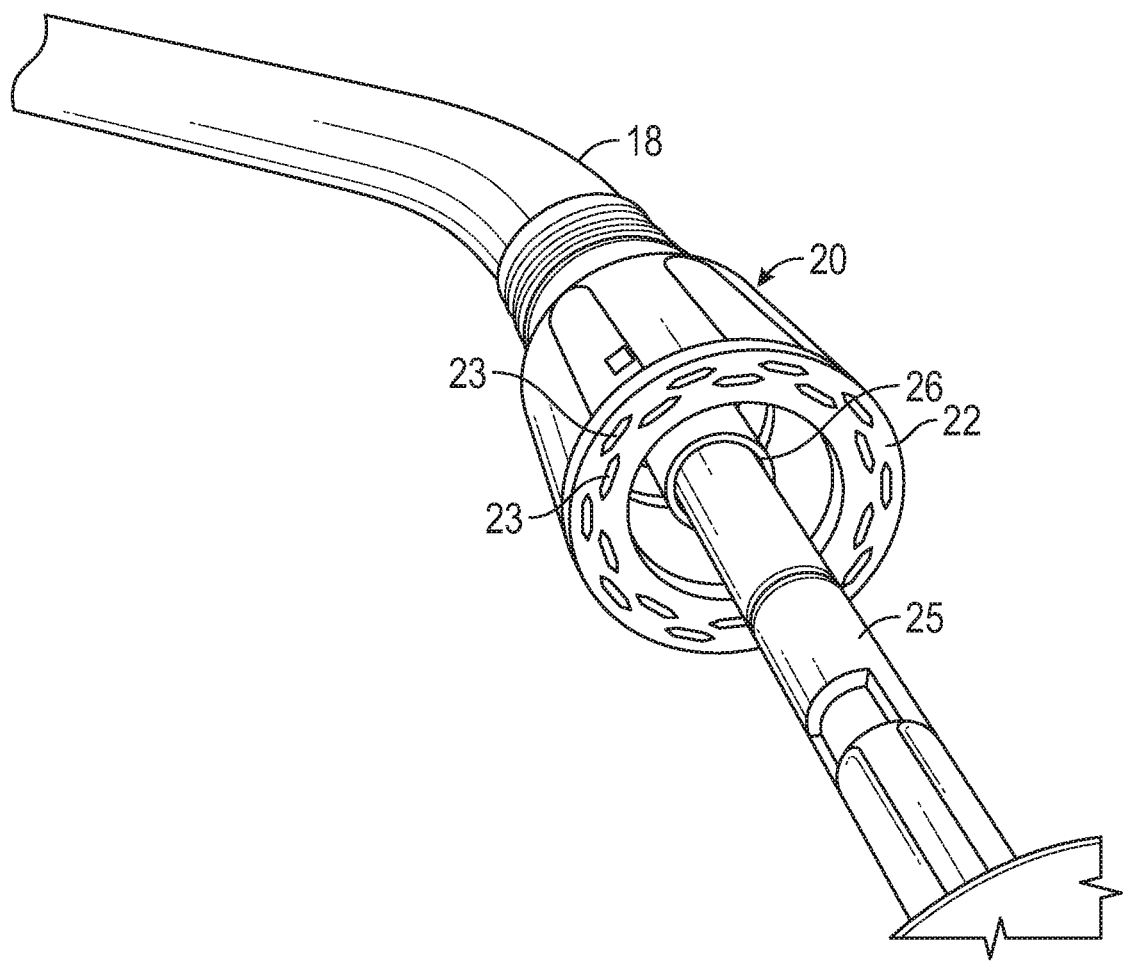
FIG. 5 is an end view of the stapler base illustrating the exit end of the passageway or channel through which gas is blown into the rectum in advance of the stapler apparatus.

Stapler shaft 18 extends from handle portion 16 up to stapler head assembly 20 at the distal end of the shaft. As is known in the field, stapler shaft 18 is designed to be inserted through the lumen of the organ which is to be stapled. Stapler head assembly 20 has a stapler head base 22 including a circular staple cartridge with openings 23 in an end wall of the base (see FIG. 5) and an anvil 24. Anvil 24 has an anvil shaft 25 which is extendable from the shaft 18 via an actuator in the handle between an advanced position (see FIG. 4) spaced from the head in which the anvil engages in an aligned end of the lumen of an organ such as the rectum or colon after surgery, and a retracted, stapling position as in FIG. 1 in which it is configured to grip end portions of a lumen to be stapled between the stapler base and anvil. A stapler actuation channel or passageway 26 extends from the handle portion up to the stapler base 22, and part of channel 26 is located in the handle as seen in FIG. 3. Gas supply inlet port 15 intersects with channel 26 in the vicinity of the actuator or trigger 30 of the handle, as seen in FIGS. 1 to 3. Apart from the intersection with inlet port 15, channel or passageway 26 is otherwise identical to stapler actuation passageways as known in the field. In one embodiment where an existing stapler device is retrofitted to include the pressurized gas supply, port 15 is formed by drilling a hole at a suitable location in the wall or shaft of handle 16 up to channel 26.

Gas supply tube 28 has an outlet end secured to the port 15 in handle 16. As illustrated in FIG. 3, a rubber sealing gasket or nipple 35 may be mounted on the end of tube 28 or in port 15 for sealing engagement between the tube and port to prevent or reduce the risk of gas leaks. No modification to the stapler shaft or channel itself is required, other than the addition of a gas inlet port in the wall of the handle portion for connection to the air supply hose. Thus, any existing EEA stapler device can be easily retrofitted to incorporate the air insufflator device, without requiring any modification to the internal design of the stapler shaft.

A conventional spring-loaded on-off valve (not illustrated) may be located at the inlet port in some embodiments, with the valve configured to open automatically in response to gas pressure and to close when the pressurized gas supply is stopped or disconnected. A pressure relief valve 34 may also be provided in the gas supply hose and configured to cut off supply of gas to the stapler channel if the air pressure exceeds a predetermined maximum value, such as 25 mm. Hg, so as to avoid or reduce the risk of excessive inflation of the rectum or colon, which may otherwise result in tearing the staple line at the end of the rectum. In some embodiments, the air or gas supply 14 may be selectively connected to port 15 by a Luer-type connector 29 or the like (see FIG. 2).

Any suitable pressurized air or gas supply device may be used, such as the manually operated air pump bulb 14 illustrated in FIG. 2. In alternative embodiments, bulb 14 may be replaced with other types of manually or automatically operated medical air or gas pumps, or tanks of pressurized gas.

The air insufflation device attached to the proximal or handle end of the stapler apparatus allows air to be introduced through the channel of the stapler shaft up to the distal end, where it exits via the stapler head openings. This stretches the rectum and rectal valves open, reducing the risk of impeding introduction of the stapler shaft to the desired location and the risk of sharp angles of the stapler head being hung up or snagged by the rectal valves, and generally allowing for smoother introduction of the stapler head and shaft along the rectum or other passageway. This may avoid the need to use gradual dilating instruments to open the passage in advance of introduction of the stapler.

In one embodiment, pressurized gas is supplied from the insufflation device to the existing stapler channel as the stapler shaft is advanced to the desired stapling site, so that air is blown into the rectum or colon while the stapler head is being positioned. Once the stapler is fired, air is again blown through the channel and out of the stapler head to test the anastomosis. Lack of any observed bubbles in the blood and fluids around the site indicates integrity of the anastomosis.

The insufflation device described above can be readily retrofitted onto any existing surgical stapler without any need to re-design the interior passageway or channel of the stapler or run any additional components such as air tubes along the length of the stapler. All that is required is to drill an air or gas inlet port transversely through the handle portion until it intersects with an existing stapler channel extending through the stapler head. In other embodiments, the surgical stapler device may be manufactured with a built in-insufflation device which may have a gas supply tube permanently or removably attached to the handle portion of the stapler to supply pressurized gas or air to the internal channel.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A method of retrofitting a surgical stapler apparatus to provide a pressurized gas supply to an internal channel extending from the handle to the stapler head of the surgical stapler apparatus, comprising:

drilling an inlet port transversely through a wall of a handle portion of a surgical stapler apparatus to intersect with an internal channel extending along the length of the surgical stapler apparatus up to the stapler head; and sealably connecting an outlet end portion of a gas supply tube connected to a supply of pressurized gas to the inlet port;

whereby pressurized gas is supplied through the gas supply tube and inlet port to the existing internal channel of the stapler apparatus and exits the channel at the stapler head to provide gas insufflation and dilation of a lumen of an abdominal organ into which the stapler shaft is inserted.

2. A method of performing a surgical stapling procedure using a surgical stapler apparatus, comprising:

inserting a stapler head and shaft of a surgical stapler apparatus into a lumen of an abdominal organ while supplying pressurized gas into a channel extending axially along the stapler shaft via a gas inlet in the handle end of the shaft to blow gas continuously through the shaft and out of the distal end of the shaft into the lumen as the stapler head and shaft is inserted;

continuing to supply pressurized gas along the channel and out of the distal end of the shaft until the stapler head reaches a surgical site for stapling;

turning off the supply of pressurized gas when the surgical site is reached;

firing the stapler head to secure tissue at the surgical site;

after firing the stapler head, supplying pressurized gas into the channel to blow gas out of the distal end of the shaft at the surgical site; and observing liquid and blood at the surgical site while air is blown out of the distal end of the shaft, whereby visible bubbles in fluid at the surgical site provide an indication of lack of integrity of an anastomosis at the surgical site.

3. The method of claim 1, wherein the internal channel comprises a stapler actuator channel.

4. The method of claim 1, wherein the surgical stapler further comprises an elongated shaft extending from the handle portion to the staple head, the elongated shaft having an inside wall surface and an outside wall surface, and wherein the internal channel is defined by the inside wall surface of the elongated shaft.

5. The method of claim 1, wherein the step of drilling the inlet port comprises drilling through a wall of the internal channel in order to intersect with the internal channel.

6. The method of claim 2, wherein the channel comprises a staple actuator channel.

\* \* \* \* \*